oxide followed by the addition of 0.5 g. of sodium borohydride. The mixture was stirred at 0° C. for one hour and then acidified with 1N-aqueous sulfuric acid. Evaporation of the methanol left 2α-carboxymethyl-3β-cyano-4α-methoxycarbonylcyclopentanol as a liquid residue which was extracted with a 20% by volume acetone in 80% ethyl acetate solution. The solution was dried and the solvent removed under reduced pressure. The residue was then dissolved in tetrahydrofuran and refluxed for 2 hours. The solvent was then removed and the residue treated with 15 ml. of water containing 2 g. of potassium bicarbonate. The solid was filtered to give 3,3a beta-4,5,6,6a beta-hexahydro-4β-cyano-2-oxo-2H-cyclopenta[b]furan-5α-carboxylic acid methylester.

EXAMPLE 28

3,3a beta-4,5,6,6a beta-hexahydro-4β-aminomethyl-2-oxo-2H-cyclopenta[b]furan-5α-carboxylic acid methylester hydrochloride 635 mg. of 3,3a beta-4,5,6,6a beta-hexahydro-4β-cyano-2-oxo-2H-cyclopenta[b]furan-5α-carboxylic acid methylester was dissolved in 100 ml. of ethanol and hydrogenated in the presence of 190 mg. of platinum oxide at room temperature in a Parrhydrogenator (53 p.s.i.) for 3½ hours. The catalyst was filtered off, the filtrate evaporated, and the free amine residue treated with ethanolic hydrogen chloride. The ethanol was removed under reduced pressure and the remaining solid suspended in an ethanol ethyl-acetate mixture and filtered give 605 mg. of 3,3a beta-4,5,6,6a beta-hexahydro-4β-aminomethyl-2-oxo-2H-cyclopenta [b]furan-5α-carboxylic acid methylester hydrochloride.

EXAMPLE 29

2-Allyl-1,3-cyclohexanedione

Allyl bromide (195 g., 1.62 mol.) was added over a 15 minute period to a stirred ice-cold mixture of cyclohexanedione (165 g., 1.47 mol.), copper-bronze (4.5 g.), and 330 ml. of 20% by weight aqueous potassium hydroxide. After 6 hours, the reaction was mixed with 1500 ml. of a 5% by weight aqueous sodium hydroxide solution and 1000 ml. of ethyl ether, filtered and the separated water layer acidified with 4N aqueous hydrochloric acid to pH 1. A brown solid (188 g.) formed upon refrigeration at 0° C. The solid was taken up in ethyl acetate and the solution was washed with water (3 × 150 ml.), dried (MgSO₄), treated with charcoal, and condensed until turbid. Upon cooling, 126 g. (57%) of 2-allyl-1,3-cyclohexanedione was collected, m.p. 125°–127° C.

EXAMPLE 30

By the procedure of Example 29, allyl bromide is reacted with 5-methyl-1,3-cyclohexanedione to produce 2-allyl-5-methyl-1,3-cyclohexanedione.

EXAMPLE 31

2-Chloro-2-allyl-1,3-cyclohexanedione t-Butylhypochlorite (104.6 g, 0196 mol) was added dropwise to a solution of 2-allyl-1,3-cyclohexanedione (132 g, 0.87 mol) in 650 ml of methanol at 0° C. The temperature was not allowed to rise above 20° C. The methanol was removed at reduced pressure in a 40° water bath and the residual oil was taken up in benzene. The benzene solution was washed with 5 percent sodium thiosulfate (3 × 250 ml), 5 percent sodium bicarbonate (3 × 250 ml) and water (1 × 250 ml). Evaporation of the benzene gave 148 g (91 percent) of 2-chloro-2-allyl-1,3-cyclohexanedione as a light yellow oil.

EXAMPLE 32

By the procedure of Example 31 2-allyl-5-methyl-1,3-cyclohexanedione was converted to 2-chloro-2-allyl-5-methyl-1,3-cyclohexanedione.

EXAMPLE 33

2-Allyl-2-cyclopenten-1-one

Anhydrous powdered sodium carbonate (670 g) and 1300 ml of dry (alumina) xylene were placed in a 3-l., three-necked flask equipped with a Dean-Stark trap, condenser, vibra-mixer, dropping funnel and argon inlet. The flask was flushed with argon and the contents brought to reflux. A solution of 2-chloro-2-allyl-1, 3-cyclohexanedione (147 g, 0.79 mol) in 200 ml of xylene was added dropwise at such a rate that strong refluxing was maintained. After 4.5 hr, the reaction was cooled, filtered, and the sodium carbonate cake washed thoroughly with ethyl acetate. Evaporation of the solvent and careful fractionization of the residual oil gave 47.8 g (50 percent) of 2-allyl-2-cyclopenten-1-one, bp 73°–84° /4.2 mm.

EXAMPLE 34

By the procedure of Example 33 2-chloro-2-allyl-5-methyl-1, 3-cyclohexanedione was converted to 2-allyl-4-methyl-2-cyclopenten-1-one.

EXAMPLE 35

2-alpha-Allyl-3-beta-nitromethylcyclopentaneone

A solution of 2-allyl-2-cyclopenten-1-one (46.8 g, 0.38 mol), 180 ml of nitromethane and 12 ml of Triton B[1] (35 percent by weight in methanol) was heated for 4 hr in an oil bath at 60°–65° C. The reaction mixture was cooled, acidified to pH 1 with 1N aqueous sulfuric acid, diluted with 500 ml of ethyl ether, washed with saturated aqueous sodium chloride solution (2 × 250 ml), and dried (MgsO₄). Evaporation of the solvent gave 69 g (100 percent) of 2-alpha-allyl-3 beta-nitromethylcyclopentaneone as a yellow oil. The compound can be further purified by distillation, bp 110°–112°/0.025 mmHg.

[1]benzyltrimethyl ammonium hydroxide

EXAMPLE 36

By the procedure of Example 35 2-allyl-4-methyl-2-cyclopenten-1-one was converted to 2-alpha-allyl-3 beta-nitromethyl-4 alpha-methylcyclopentan-1-one.

EXAMPLE 37

2-alpha-Carboxymethyl-3 beta-nitromethylcyclopentan-1-one

A solution of sodium permanganate (52.2 g, 0.26 mol) in 140 ml of water was added dropwise over a 1 hr period to a rapidly stirred mixture of 2-alpha-allyl-3 beta-nitromethylcyclopentaneone (18.3 g, 0.1 mol), 300 ml of acetone, and 83 ml of 10 percent (v/v) sulfuric acid under argon at −10°–0°. The reaction was stirred an additional 45 min at 0° C., then saturated with sodium chloride and extracted with 3:7 tetahydrofuran-methylene chloride. The combined organic extracts were dried (MgSO₄O) and evaporated to give 23.2 g of crude 2 alpha-carboxymethyl-3 beta-nitromethylcyclo-

PROCESS FOR THE MANUFACTURE OF MALEIC ANHYDRIDE

REFERENCE TO A RELATED APPLICATION

This is a continuation-in-part of copending application Ser. No. 525,599 filed Nov. 20, 1974 and now abandoned. The entire disclosure of said related application is relied on herein.

The present invention relates to a process for the manufacture of maleic anhydride.

Catalysts for the oxidation of benzene to maleic anhydride are already known. They are formed from mixtures of vanadium and molybdenum oxides to which may be added in smaller proportions other mineral oxides in order to improve the performance of the catalyst. These complex mixtures of oxides may be deposited on various supports, generally based on alumina or silica, or may be used as such in the form of powder, grains or agglomerates.

We have now found that excellent results are obtained in the oxidation of benzene to maleic anhydride if a catalyst is used which comprises an inert support coated with a catalytically active mass containing 10% to 20% by weight of antimony trioxide, 40% to 70% by weight of vanadium pentoxide 20% to 50% by weight of molybdenum trioxide, 0.7% to 1.5% of phosphorus pentoxide, 0.9% to 2.0% by weight of sodium oxide and possibly an other mineral oxide.

Such a catalyst, compared with the known catalysts, shows improved activity, selectivity and length of life. Industrially, this is manifested both by an increased yield of maleic anhydride with respect to the benzene used and by the possibility of operating with high concentrations of benzene in air, e.g. one mole of benzene per 10 to 16 moles of oxygen, during its passage over the catalyst. Further if the intrinsic qualities of the catalyst remain unchanged for many months, the production of maleic anhydride with relation to the volume of catalyst used is very high e.g. 120 to 150 g per hour for each liter of catalyst.

According to the present invention therefore a process for the manufacture of maleic anhydride by the oxidation of benzene with oxygen in the presence of a catalyst which has been previously activated is provided in which the catalyst comprises an inert support coated with a catalytically active mass containing, by weight 10% to 20% of antimony trioxide, 40% to 70% of vanadium pentoxide, 20% to 50% of molybdenum trioxide,, 0.7 to 1.5% of phosphorus pentoxide, 0.9 to 2.0% of sodium oxide and possibly another mineral oxide.

In addition to the antimony trioxide, vanadium pentoxide, molybdenum trioxide, phosphorus pentoxide and sodium oxide, the catalytically active mass may contain various oxides such as for example the oxides of nickel, calcium, iron, silver, strontium, uranium, tungsten, cobalt or boron.

In the catalysts according to the invention, the catalytically active mass preferably represents 10% to 20% of the total weight of the catalyst. The latter is preferably in the form of spherically or irregularly-shaped grains of which the average particle size is from 3 to 8 mm.

The inert support may for example comprise an aluminium and/or silicon derivative or a mixture of such derivatives. Examples of such inert supports are alumina, silica, aluminium silicate and silicon carbide.

The catalysts according to the invention may be prepared by known techniques. Thus, for example, the oxides of the catalytically active mass and/or the corresponding salts may be dissolved or suspended in water or in an organic solvent and projected on to the inert support placed in a coating apparatus maintained at a temperature sufficient to allow the evaporation of the water or the solvent as the solution or suspension is deposited on the support. Alternatively, the inert support and the liquid mixture may, for example be mixed in a heated coating drum and the mixture evaporated to dryness. The coated support is then calcined in the presence of a slight excess of air in the coating apparatus itself or in a muffle furnace at a temperature of 400° C. to 500° C. for at least 2 hours.

The catalysts must be kept out of contact with air and moisture until they are used. When they are used, the catalysts must be previously activated by heating in the presence of air at a temperature of from 300° C. to 600° C. for 6 to 24 hours.

In a preferred embodiment of the invention the oxidation of benzene is effected in a tube of inside diameter 21 mm, and maintained at a temperature of from 300° C. to 400° C. by an isothermal bath. The hot point of the catalyst is maintained at a temperature of from 400° C to 450° C., preferably at about 430° C. 10 to 16 moles of oxygen are used per mole of benzene, and the oxygen is preferably applied in the form of air at atmospheric pressure or under a slight superatmospheric pressure which may go up to 2 atmospheres.

The invention is illustrated by the following Examples. In these Examples the sodium oxide originates from the sodium phosphate.

EXAMPLE 1

800 g. of silicon carbide in spherical grains 6 mm in diameter obtained by fritting are introduced into a 2-liter coating apparatus. The grains are heated to about 180° C. and then a solution of 45.5 g. of ammonium paramolybdate, 84 g. of ammonium metavanadate, 8.4 g. of trisodium phosphate and 20 g. of antimony oxide in 690 g. of 33% concentrated hydrochloric acid, is sprayed on their surface in a period of about 1 hour. When the spraying is finished, the grains are heated to 410° C. and maintained at this temperature for 4 hours under a slight current of air. A catalyst having the following composition by weight is thus obtained:

Silicon carbide (as support): — 86.38%
Molybdenum trioxide: — 4.00%
Vanadium pentoxide: — 7.07%
Phosphorus pentoxide: — 0.17%
Antimony trioxide: — 2.16%
Sodium oxide — 0.22%

This catalyst is introduced into a vertical steel tube with an inside diameter of 21 mm, placed in a "salt bath" comprising a mixture of equal parts of potassium nitrate and sodium nitrite. This bath is stirred and raised to a temperature of 350° C. and to effect activation of the catalyst a stream of air heated to 150° C. is passed into the tube at 2000 g/hour and in a period of 10 hours the temperature of the salt bath is taken to 420° C. This temperature and the stream of air are then maintained for 12 hours.

After having lowered the temperature of the salt bath to 370° C. a mixture of 150 g/hour of benzene and 3300 g/hour of air is circulated in the tube. A production of 142 g/hour of maleic anhydride, i.e. 147 g/hour/liter of catalyst, is thus obtained at the outlet of the reaction and the combined methylene chloride solution washed with dilute hydrochloric acid to remove any remaining pyridine. The methylene chloride was then removed under reduced pressure and the residue treated with 50 ml of 3:1 parts by volume acetic acid/water solution at 35° C. for 15 hr. The solvents were then removed under high vacuum and the residue purified by column chromatography to give 7-[3 alpha-methyl-5-oxo-2 beta(3 alpha-hydroxy-1-trans-octenyl) cyclopentyl]cis-5-heptenoic acid.

EXAMPLE 56

By the procedure of Example 55, 7 [[5-alpha-hydroxy-2 beta [3 alpha-(2-tetrahydropyranyloxy)-1-trans-octenyl[cyclopentyl]-cis-5-heptenoic acid was converted to 7[5-oxo-2 beta(3 alpha-hydroxy-1-trans-octenyl)cyclopenyl]cis-5-heptenoic acid.

EXAMPLE 57

7[3 alpha-Methyl-5 alpha-hydroxy-2 beta(3 alpha-hydroxy-1-trans-octenyl)cyclopentyl]cis-5-heptenoic acid A solution of 200 mg of 7-[[3 alpha-methyl-5 alpha-hydroxy-2 beta[3 alpha-(2-tetrapyranyloxy)-1-trans-octenyl]cyclopentyl]]cis-5-heptenoic acid in 5 ml of a 3:1 parts by volume acetic acid/ water solution was kept at 35° C. for 15 hr. The solvent was then removed under high vacuum and the residue purified via column chromatography to give 7[3 alpha-methyl-5 alpha-hydroxy-2 beta(3 alpha-hydroxy-1-trans-octenyl)cyclopentyl]cis-5-heptenoic acid.

EXAMPLE 58

By the procedure of Example 57, 7[[5 alpha-hydroxy-2 beta ['alpha-(2-tetrahydropyranyloxy)-1-trans-octenyl]cyclopentyl]]cis-5-heptenoic acid was converted to 7[3 alpha-hydroxy-2 beta (3 alpha-hyroxy-1-trans-octenyl)cyclopentyl]cis-5-heptenoic acid.

We claim:
1. A compound of the formula:

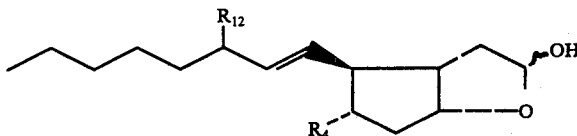

wherein $R_4$ lower alkyl; and $R_{12}$ is lower alkanoyloxy, benzoyloxy, tetrahydropyranyloxy, benzyloxy, trityloxy, 4-methoxy-5,6-dihydro-2H-pyranyloxy, benzyhydryloxy or trimethylsilyloxy or enantiomers or racemates thereof.

2. The compound of claim 1 wherein said compound is 3,3a beta-4,5,6,6a beta-hexahydro-4beta [3 alpha (2-tetrahydropyranyloxy)-1-transoctenyl] 5 alpha-methyl-2-hydroxy-2H-cyclopenta[b] furan.

* * * * *